United States Patent
Gusmeroli et al.

(10) Patent No.: US 9,040,457 B2
(45) Date of Patent: May 26, 2015

(54) PHENYLAMIDINES HAVING A HIGH FUNGICIDAL ACTIVITY AND USE THEREOF

(75) Inventors: Marilena Gusmeroli, Monza (IT); Lucio Filippini, Novara (IT); Franco Pellacini, Milan (IT); Paolo Bravini, Novara (IT); Alexia Elmini, Buronzo (IT); Matteo Santino Vazzola, Cogliate (IT); Christian Badaracco, Vittuone (IT)

(73) Assignee: ISAGRO S.P.A., Milan (IT)

( * ) Notice: Subject to any disclaimer, the term of this patent is extended or adjusted under 35 U.S.C. 154(b) by 98 days.

(21) Appl. No.: 13/818,622

(22) PCT Filed: Aug. 18, 2011

(86) PCT No.: PCT/EP2011/064210
§ 371 (c)(1),
(2), (4) Date: Feb. 22, 2013

(87) PCT Pub. No.: WO2012/025450
PCT Pub. Date: Mar. 1, 2012

(65) Prior Publication Data
US 2013/0157851 A1    Jun. 20, 2013

(30) Foreign Application Priority Data
Aug. 23, 2010  (IT) .............................. MI2010A1564

(51) Int. Cl.
| | |
|---|---|
| *C07C 323/41* | (2006.01) |
| *A01N 37/52* | (2006.01) |
| *A01N 43/36* | (2006.01) |
| *A01N 43/40* | (2006.01) |
| *A01N 43/54* | (2006.01) |
| *A01N 43/56* | (2006.01) |
| *A01N 43/58* | (2006.01) |
| *A01N 43/84* | (2006.01) |
| *C07D 213/70* | (2006.01) |
| *C07D 231/44* | (2006.01) |
| *C07D 237/18* | (2006.01) |
| *C07D 239/56* | (2006.01) |
| *C07D 241/18* | (2006.01) |
| *C07D 295/13* | (2006.01) |
| *A01N 43/60* | (2006.01) |
| *C07D 295/195* | (2006.01) |

(52) U.S. Cl.
CPC .............. *C07C 323/41* (2013.01); *A01N 37/52* (2013.01); *A01N 43/36* (2013.01); *A01N 43/40* (2013.01); *A01N 43/54* (2013.01); *A01N 43/56* (2013.01); *A01N 43/58* (2013.01); *A01N 43/84* (2013.01); *C07C 2101/02* (2013.01); *C07D 213/70* (2013.01); *C07D 231/44* (2013.01); *C07D 237/18* (2013.01); *C07D 239/56* (2013.01); *C07D 241/18* (2013.01); *C07D 295/13* (2013.01); *A01N 43/60* (2013.01); *C07D 295/195* (2013.01)

(58) Field of Classification Search
CPC ....... A01N 37/52; A01N 43/40; A01N 43/54; C07D 295/195
USPC ........................... 504/101, 358; 514/238, 247
See application file for complete search history.

(56) References Cited

U.S. PATENT DOCUMENTS

2010/0113276 A1 *   5/2010  Kuhn et al. ................... 504/242

FOREIGN PATENT DOCUMENTS

| WO | 0046184 A1 | 8/2000 |
|---|---|---|
| WO | 2007031523 A1 | 3/2007 |
| WO | 2007031524 A1 | 3/2007 |
| WO | 2008110278 A2 | 9/2009 |

OTHER PUBLICATIONS

International Search Report Dated Sep. 28, 2011.

* cited by examiner

*Primary Examiner* — Ali Soroush
*Assistant Examiner* — Yanzhi Zhang
(74) *Attorney, Agent, or Firm* — Hedman & Costigan, P.C.; James V. Costigan; Kathleen A. Costigan

(57) ABSTRACT

New phenylamidines are described, having general formula (I):

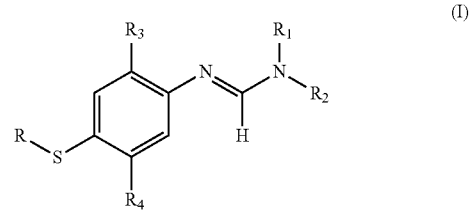

and their use for the control of phytopathogenic fungi.

15 Claims, No Drawings

PHENYLAMIDINES HAVING A HIGH FUNGICIDAL ACTIVITY AND USE THEREOF

The present invention relates to phenylamidines having a high fungicidal activity and their relative use, in particular substituted phenylamidines having a high fungicidal activity and their use for the control of phytopathogenic fungi of important agricultural crops.

Phenylamidines having a high fungicidal activity are described in international patent applications WO 2000/46184, WO 2003/093224, WO 2007/031508, WO 2007/031512, WO 2007/031513, WO 2007/031523, WO 2007/031524, WO 2008/110279.

The products described in these documents, however, are often unsatisfactory from the point of view of both the level of activity with respect to phytopathogenic fungi and also, or alternatively, from the point of view of phytotoxicity with respect to important agricultural crops.

In particular, for example, the compounds N-ethyl-N-methyl-N'-[4-(3-trifluoromethylphenoxy)-2,5-xilyl]-formamidine, N,N-dimethyl-N'-[4-(3-trifluoromethylphenoxy)-2,5-xilyl]formamidine, N,N-dimethyl-N'-[4-(3-trifluoromethoxyphenoxy)-2,5-xilyl]formamidine, N,N-dimethyl-N'-[4-(3-trifluoroethoxyphenoxy)-2,5-xilyl]-formamidine, described in international patent application WO 00/46184, at the doses which allow a good fungicidal activity to be obtained, show a marked leaf necrosis on cereals, cucumbers, tomatoes and other important crops: this effect makes their use as fungicides practically unacceptable. On the other hand, the compound N,N-dimethyl-N'-[4-(3-trifluoromethylphenylthio)-2,5-xilyl]formamidine, also described in international patent application WO 00/46184, proves to be insufficient from the point of view of fungicidal activity, which is only exerted satisfactorily in excessively high dosages.

International patent application WO 2008/110278 describes a whole series of (hetero)aryloxy- and (hetero)arylthio N,N-dialkyl-N'-phenyl-formamidines with a herbicidal activity, variously substituted on the (hetero)aryloxy and (hetero)arylthio rings.

The Applicant has now surprisingly found that new phenylamidines characterized by a (hetero)arylthio group in position 4 of the phenyl, and by particular combinations of substituents on the (hetero)arylthio ring and on the nitrogen atom, not only exert an excellent fungicidal activity at low doses, but are also well tolerated by many vegetable species, thus allowing the practical use of these compounds for the control of phytopathogenic microorganisms of important agricultural crops.

An object of the present invention therefore relates to new phenylamidines having general formula (I):

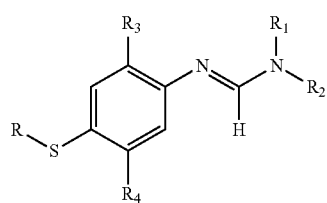

wherein

R represents a phenyl, pyridyl, pyrimidyl, pyrazyl or pyridazyl group, all groups substituted by at least a substituent selected from $C_1$-$C_6$ polyfluoroalkoxy containing at least one hydrogen atom, $C_1$-$C_6$ polyfluoroalkylthio containing at least one hydrogen atom, $C_3$-$C_6$ cycloalkyl, $C_3$-$C_6$ halocycloalkyl, $C_3$-$C_6$ cycloalkoxy, $C_3$-$C_6$ halocycloalkoxy, $C_4$-$C_8$ cycloalkylalkoxy, $C_4$-$C_8$ halocycloalkylalkoxy; said groups phenyl, pyridyl, pyrimidyl, pyrazyl or pyridazyl being optionally substituted by one or two further substituents, equal to or different from each other, selected from halogen atom, $C_1$-$C_6$ alkyl, $C_1$-$C_6$ haloalkyl;

$R_1$ represents $C_2$-$C_6$ alkyl;

$R_2$ represents $C_1$-$C_6$ alkyl; or $R_1$ and $R_2$, together with the N atom to which they are bound, form a heterocyclic ring containing from 4 to 7 atoms, optionally substituted by halogen atoms;

$R_3$ and $R_4$, equal to or different from each other, represent a hydrogen atom, a halogen atom, a $C_1$-$C_6$ alkyl, a $C_1$-$C_6$ alkoxy, a $C_1$-$C_6$ haloalkoxy, a $CF_3$ group, a $CF_2H$ group, a $CFH_2$ group, a cyano group.

Examples of halogen are fluorine, chlorine, bromine, iodine.

Examples of $C_1$-$C_6$ alkyl are methyl, ethyl, n-propyl, iso-propyl, n-butyl, isobutyl, sec-butyl, tertbutyl, n-pentyl, 3-methylbutyl, n-hexyl, 3,3-dimethylbutyl.

Examples of $C_1$-$C_6$ haloalkyl are fluoromethyl, difluoromethyl, trifluoromethyl, chloromethyl, dichloro-methyl, 2,2,2-trifluoroethyl, 1,1,2,2-tetrafluoroethyl, pentafluoroethyl, heptafluoropropyl, 4,4,4-trichloro-butyl, 4,4-difluoropentyl, 5,5-difluorohexyl.

Examples of $C_1$-$C_6$ polyfluoroalkoxy group containing at least one hydrogen atom are difluoromethoxy, 2,2,2-trifluoroethoxy, 1,1,2,2-tetrafluoroethoxy, 2,2,3,3-tetrafluoropropoxy, 2,2,3,3,3-pentafluoropropoxy, 1,1,2,3,3,3-hexafluoropropoxy, 2,2,3,4,4,4-hexafluorobutoxy, 4,4-difluoropentoxy, 4,4,5,5,5-pentafluoropentoxy, 2,2,3,3,4,4,5,5-octafluoropentoxy, 5,5-difluorohexyloxy.

Examples of $C_1$-$C_6$ polyfluoroalkylthio group containing at least one hydrogen atom are difluoromethylthio, 2,2,2-trifluoroethylthio, 1,1,2,2-tetrafluoroethylthio, 2,2,3,3-tetrafluoropropylthio, 2,2,3,3,3-pentafluoropropylthio, 1,1,2,3,3,3-hexafluoropropylthio, 2,2,3,4,4,4-hexafluorobutylthio, 4,4-difluoropentylthio, 4,4,5,5,5-pentafluoropentylthio, 2,2,3,3,-4,4,5,5-octafluoropentylthio, 5,5-difluorohexylthio.

Examples of $C_3$-$C_6$ cycloalkyl are cyclopropyl, cyclobutyl, cyclopentyl, cyclohexyl.

Examples of a $C_3$-$C_6$ halocycloalkyl are 2,2-dichlorocyclopropyl, 2,2-difluorocyclopropyl, 2,2,3,3-tetrafluorocyclobutyl, 3,3-difluorocyclopentyl, 2-fluorocyclohexyl.

Examples of $C_3$-$C_6$ cycloalkoxy are cyclopropoxy, cyclobutoxy, cyclopentoxy, cyclohexyloxy.

Examples of $C_3$-$C_6$ halocycloalkoxy are 2,2-dichlorocyclopropoxy, 2,2-difluorocyclopropoxy, 2,2,-3,3-tetrafluorocyclobutoxy, 3,3-difluorocyclopentoxy, 2-fluorocyclohexyloxy.

Examples of $C_4$-$C_8$ cycloalkylalkoxy are cyclopropylmethoxy, cyclobutylmethoxy, cyclopentylmethoxy, cyclohexylmethoxy, cyclohexylethoxy.

Examples of $C_4$-$C_8$ halocycloalkylalkoxy are 2,2-dichlorocyclopropylmethoxy, 2,2-difluorocyclopropylmethoxy, 2,2,3,3-tetrafluorocyclobutylmethoxy, 3,3-difluorocyclopentylmethoxy, 4,4-difluorocyclohexylmethoxy, 4,4-difluorocyclohexylethoxy.

Examples of heterocyclic rings with from 4 to 7 atoms optionally halogenated are: azetidine, 3,3-difluoroazetidine, pyrrolidine, piperidine, 4-fluoropiperidine, morpholine.

Representative examples of compounds having general formula (I) are those wherein R, $R_1$, $R_2$, $R_3$ and $R_4$ have the meanings indicated in Table 1.

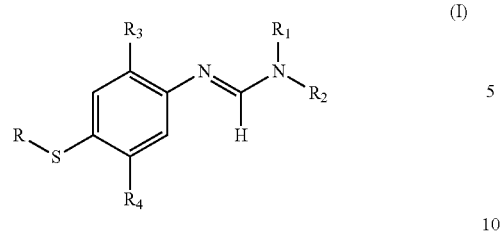

(I)

TABLE 1

| R | $R_1$ | $R_2$ | $R_3$ | $R_4$ |
|---|---|---|---|---|
| 3-$HCF_2CF_2O$-phenyl | Et | Me | Me | Me |
| 3-$HCF_2CF_2S$-phenyl | Et | Me | Me | Me |
| 3-$HCF_2CF_2O$-phenyl | i-Pr | Me | Me | Me |
| 3-$HCF_2CF_2O$-phenyl | n-Pr | Me | Me | Me |
| 3-$HCF_2CF_2O$-phenyl | —$(CH_2)_4$— | | Me | Me |
| 3-$HCF_2CF_2O$-phenyl | —$(CH_2)_5$— | | Me | Me |
| 3-$HCF_2CF_2O$-phenyl | —$CH_2CH_2OCH_2CH_2$— | | Me | Me |
| 3-$HCF_2CF_2O$-phenyl | Et | Me | H | Me |
| 3-$HCF_2CF_2O$-phenyl | Et | Me | Me | $CF_3$ |
| 3-$HCF_2CF_2O$-phenyl | Et | Me | Me | $CF_2H$ |
| 3-$HCF_2CF_2O$-phenyl | Et | Me | H | $CF_3$ |
| 3-$HCF_2CF_2O$-phenyl | Et | Me | $CF_2H$ | Me |
| 3-$HCF_2CF_2O$-phenyl | Et | Me | Cl | Cl |
| 3-$HCF_2CF_2O$-phenyl | Et | Me | Me | Cl |
| 3-$HCF_2CF_2O$-phenyl | Et | Me | Me | H |
| 3-$HCF_2CF_2O$-phenyl | Et | Me | H | Me |
| 3-$HCF_2CF_2O$-phenyl | Et | Me | Me | CN |
| 3-$HCF_2CF_2O$-phenyl | Et | Me | Me | OMe |
| 3-$HCF_2CF_2S$-phenyl | Et | Me | Me | Me |
| 4-$HCF_2CF_2O$-phenyl | Et | Me | Me | Me |
| 4-$HCF_2CF_2O$-phenyl | —$(CH_2)_4$— | | Me | Me |
| 4-$HCF_2CF_2O$-phenyl | —$(CH_2)_5$— | | Me | Me |
| 4-$HCF_2CF_2O$-phenyl | —$CH_2CH_2OCH_2CH_2$— | | Me | Me |
| 4-$HCF_2CF_2S$-phenyl | Et | Me | Me | Me |
| 3-$HCF_2O$-phenyl | Et | Me | Me | Me |
| 3-$HCF_2O$-phenyl | —$(CH_2)_4$— | | Me | Me |
| 3-$HCF_2O$-phenyl | —$(CH_2)_5$— | | Me | Me |
| 3-$HCF_2O$-phenyl | —$CH_2CH_2OCH_2CH_2$— | | Me | Me |
| 3-$HCF_2S$-phenyl | Et | Me | Me | Me |
| 4-$HCF_2O$-phenyl | Et | Me | Me | Me |
| 4-$HCF_2O$-phenyl | —$(CH_2)_4$— | | Me | Me |
| 4-$HCF_2O$-phenyl | —$(CH_2)_5$— | | Me | Me |
| 4-$HCF_2O$-phenyl | —$CH_2CH_2OCH_2CH_2$— | | Me | Me |
| 4-$HCF_2S$-phenyl | Et | Me | Me | Me |
| 3-$CF_3CH_2O$-phenyl | Et | Me | Me | Me |
| 3-$CF_3CH_2O$-phenyl | —$(CH_2)_4$— | | Me | Me |
| 3-$CF_3CH_2O$-phenyl | —$(CH_2)_5$— | | Me | Me |
| 3-$CF_3CH_2O$-phenyl | —$CH_2CH_2OCH_2CH_2$— | | Me | Me |
| 3-$CF_3CH_2S$-phenyl | Et | Me | Me | Me |
| 4-$CF_3CH_2O$-phenyl | Et | Me | Me | Me |
| 4-$CF_3CH_2O$-phenyl | —$(CH_2)_5$— | | Me | Me |
| 3-$HCF_2CF_2CH_2O$-phenyl | Et | Me | Me | Me |
| 3-$HCF_2CF_2CH_2O$-phenyl | —$(CH_2)_4$— | | Me | Me |
| 3-$HCF_2CF_2CH_2O$-phenyl | —$(CH_2)_5$— | | Me | Me |
| 3-$HCF_2CF_2CH_2O$-phenyl | —$CH_2CH_2OCH_2CH_2$— | | Me | Me |
| 4-$HCF_2CF_2CH_2O$-phenyl | Et | Me | Me | Me |
| 3-$HCF_2CF_2CH_2S$-phenyl | Et | Me | Me | Me |
| 4-$HCF_2CF_2CH_2O$-phenyl | —$(CH_2)_4$— | | Me | Me |
| 4-$HCF_2CF_2CH_2O$-phenyl | —$(CH_2)_5$— | | Me | Me |
| 4-$HCF_2CF_2CH_2O$-phenyl | —$CH_2CH_2OCH_2CH_2$— | | Me | Me |
| 3-$CF_3CF_2CH_2O$-phenyl | Et | Me | Me | Me |
| 3-$CF_3CF_2CH_2O$-phenyl | —$(CH_2)_4$— | | Me | Me |
| 3-$CF_3CF_2CH_2O$-phenyl | —$(CH_2)_5$— | | Me | Me |
| 4-$CF_3CF_2CH_2O$-phenyl | Et | Me | Me | Me |
| 4-$CF_3CF_2CH_2O$-phenyl | —$(CH_2)_4$— | | Me | Me |
| 4-$CF_3CF_2CH_2O$-phenyl | —$(CH_2)_5$— | | Me | Me |
| 3-$CF_3CHFCF_2O$-phenyl | Et | Me | Me | Me |
| 4-$CF_3CHFCF_2O$-phenyl | Et | Me | Me | Me |
| 3-$CF_3CHFCF_2CH_2O$-phenyl | Et | Me | Me | Me |
| 4-$CF_3CHFCF_2CH_2O$-phenyl | Et | Me | Me | Me |
| 3-$HCF_2CF_2CF_2CF_2CH_2O$-phenyl | Et | Me | Me | Me |
| 4-$HCF_2CF_2CF_2CF_2CH_2O$-phenyl | Et | Me | Me | Me |
| 4-F-3-$HCF_2O$-phenyl | Et | Me | Me | Me |

TABLE 1-continued

| R | $R_1$ | $R_2$ | $R_3$ | $R_4$ |
|---|---|---|---|---|
| 4-F-3-$HCF_2$O-phenyl | —$(CH_2)_5$— | | Me | Me |
| 4-Cl-3-$HCF_2$O-phenyl | Et | Me | Me | Me |
| 4-Cl-3-$HCF_2$O-phenyl | —$(CH_2)_5$— | | Me | Me |
| 4-Me-3-$HCF_2$O-phenyl | Et | Me | Me | Me |
| 2,4-$F_2$-3-$HCF_2$O-phenyl | Et | Me | Me | Me |
| 4,5-$F_2$-3-$HCF_2$O-phenyl | Et | Me | Me | Me |
| 2-F-3-$HCF_2$O-phenyl | Et | Me | Me | Me |
| 5-F-3-$HCF_2$O-phenyl | Et | Me | Me | Me |
| 3-F-4-$HCF_2$O-phenyl | Et | Me | Me | Me |
| 3-F-4-$HCF_2$O-phenyl | —$(CH_2)_5$— | | Me | Me |
| 3-Cl-4-$HCF_2$O-phenyl | Et | Me | Me | Me |
| 3-Cl-4-$HCF_2$O-phenyl | —$(CH_2)_5$— | | Me | Me |
| 3-Me-4-$HCF_2$O-phenyl | Et | Me | Me | Me |
| 3-$CF_3$-4-$HCF_2$O-phenyl | Et | Me | Me | Me |
| 2-F-4-$HCF_2$O-phenyl | Et | Me | Me | Me |
| 2-Cl-4-$HCF_2$O-phenyl | Et | Me | Me | Me |
| 3,5-$F_2$-4-$HCF_2$O-phenyl | Et | Me | Me | Me |
| 4-F-3-$HCF_2CF_2$O-phenyl | Et | Me | Me | Me |
| 4-F-3-$HCF_2CF_2$O-phenyl | —$(CH_2)_5$— | | Me | Me |
| 4-Cl-3-$HCF_2CF_2$O-phenyl | Et | Me | Me | Me |
| 4-Cl-3-$HCF_2CF_2$O-phenyl | —$(CH_2)_5$— | | Me | Me |
| 4-Me-3-$HCF_2CF_2$O-phenyl | Et | Me | Me | Me |
| 2,4-$F_2$-3-$HCF_2CF_2$O-phenyl | Et | Me | Me | Me |
| 4,5-$F_2$-3-$HCF_2CF_2$O-phenyl | Et | Me | Me | Me |
| 2-F-3-$HCF_2CF_2$O-phenyl | Et | Me | Me | Me |
| 5-F-3-$HCF_2CF_2$O-phenyl | Et | Me | Me | Me |
| 3-F-4-$HCF_2CF_2$O-phenyl | Et | Me | Me | Me |
| 3-F-4-$HCF_2CF_2$O-phenyl | —$(CH_2)_5$— | | Me | Me |
| 3-Cl-4-$HCF_2CF_2$O-phenyl | Et | Me | Me | Me |
| 3-Cl-4-$HCF_2CF_2$O-phenyl | —$(CH_2)_5$— | | Me | Me |
| 3-Me-4-$HCF_2CF_2$O-phenyl | Et | Me | Me | Me |
| 3-$CF_3$-4-$HCF_2CF_2$O-phenyl | Et | Me | Me | Me |
| 2-F-4-$HCF_2CF_2$O-phenyl | Et | Me | Me | Me |
| 2-Cl-4-$HCF_2CF_2$O-phenyl | Et | Me | Me | Me |
| 3,5-$F_2$-4-$HCF_2CF_2$O-phenyl | Et | Me | Me | Me |
| 4-F-3-$CF_3CH_2$O-phenyl | Et | Me | Me | Me |
| 4-F-3-$CF_3CH_2$O-phenyl | —$(CH_2)_5$— | | Me | Me |
| 4-Cl-3-$CF_3CH_2$O-phenyl | Et | Me | Me | Me |
| 4-Cl-3-$CF_3CH_2$O-phenyl | —$(CH_2)_5$— | | Me | Me |
| 4-Me-3-$CF_3CH_2$O-phenyl | Et | Me | Me | Me |
| 2,4-$F_2$-3-$CF_3CH_2$O-phenyl | Et | Me | Me | Me |
| 4,5-$F_2$-3-$CF_3CH_2$O-phenyl | Et | Me | Me | Me |
| 2-F-3-$CF_3CH_2$O-phenyl | Et | Me | Me | Me |
| 5-F-3-$CF_3CH_2$O-phenyl | Et | Me | Me | Me |
| 3-F-4-$CF_3CH_2$O-phenyl | Et | Me | Me | Me |
| 3-F-4-$CF_3CH_2$O-phenyl | —$(CH_2)_5$— | | Me | Me |
| 3-Cl-4-$CF_3CH_2$O-phenyl | Et | Me | Me | Me |
| 3-Cl-4-$CF_3CH_2$O-phenyl | —$(CH_2)_5$— | | Me | Me |
| 3-Me-4-$CF_3CH_2$O-phenyl | Et | Me | Me | Me |
| 2-F-4-$CF_3CH_2$O-phenyl | Et | Me | Me | Me |
| 2-Cl-4-$CF_3CH_2$O-phenyl | Et | Me | Me | Me |
| 3,5-$F_2$-4-$CF_3CH_2$O-phenyl | Et | Me | Me | Me |
| 4-F-3-$HCF_2CF_2CH_2$O-phenyl | Et | Me | Me | Me |
| 4-F-3-$HCF_2CF_2CH_2$O-phenyl | —$(CH_2)_5$— | | Me | Me |
| 4-Cl-3-$HCF_2CF_2CH_2$O-phenyl | Et | Me | Me | Me |
| 4-Cl-3-$HCF_2CF_2CH_2$O-phenyl | —$(CH_2)_5$— | | Me | Me |
| 4-Me-3-$HCF_2CF_2CH_2$O-phenyl | Et | Me | Me | Me |
| 2,4-$F_2$-3-$HCF_2CF_2CH_2$O-phenyl | Et | Me | Me | Me |
| 4,5-$F_2$-3-$HCF_2CF_2CH_2$O-phenyl | Et | Me | Me | Me |
| 2-F-3-$HCF_2CF_2CH_2$O-phenyl | Et | Me | Me | Me |
| 5-F-3-$HCF_2CF_2CH_2$O-phenyl | Et | Me | Me | Me |
| 3-F-4-$HCF_2CF_2CH_2$O-phenyl | Et | Me | Me | Me |
| 3-F-4-$HCF_2CF_2CH_2$O-phenyl | —$(CH_2)_5$— | | Me | Me |
| 3-Cl-4-$HCF_2CF_2CH_2$O-phenyl | Et | Me | Me | Me |
| 3-Cl-4-$HCF_2CF_2CH_2$O-phenyl | —$(CH_2)_5$— | | Me | Me |
| 3-Me-4-$HCF_2CF_2CH_2$O-phenyl | Et | Me | Me | Me |
| 2-F-4-$HCF_2CF_2CH_2$O-phenyl | Et | Me | Me | Me |
| 2-Cl-4-$HCF_2CF_2CH_2$O-phenyl | Et | Me | Me | Me |
| 3,5-$F_2$-4-$HCF_2CF_2CH_2$O-phenyl | Et | Me | Me | Me |
| 5-$HCF_2CF_2$O-2-pyridyl | Et | Me | Me | Me |
| 5-$HCF_2$O-2-pyridyl | Et | Me | Me | Me |
| 5-$CF_3CH_2$O-2-pyridyl | Et | Me | Me | Me |
| 5-$HCF_2CF_2CH_2$O-2-pyridyl | Et | Me | Me | Me |
| 2-$HCF_2CF_2$O-4-pyridyl | Et | Me | Me | Me |
| 2-$HCF_2$O-4-pyridyl | Et | Me | Me | Me |
| 2-$CF_3CH_2$O-4-pyridyl | Et | Me | Me | Me |
| 2-$HCF_2CF_2CH_2$O-4-pyridyl | Et | Me | Me | Me |
| 2-$HCF_2CF_2$O-5-pyridyl | Et | Me | Me | Me |

TABLE 1-continued

| R | R₁ | R₂ | R₃ | R₄ |
|---|---|---|---|---|
| 2-HCF₂O-5-pyridyl | Et | Me | Me | Me |
| 2-CF₃CH₂O-5-pyridyl | Et | Me | Me | Me |
| 2-HCF₂CF₂O-5-pyrimidyl | Et | Me | Me | Me |
| 2-HCF₂O-5-pyrimidyl | Et | Me | Me | Me |
| 2-CF₃CH₂O-5-pyrimidyl | Et | Me | Me | Me |
| 5-HCF₂CF₂O-2-pyrazyl | Et | Me | Me | Me |
| 5-HCF₂O-2-pyrazyl | Et | Me | Me | Me |
| 5-CF₃CH₂O-2-pyrazyl | Et | Me | Me | Me |
| 6-HCF₂CF₂O-3-pyridazyl | Et | Me | Me | Me |
| 6-HCF₂O-3-pyridazyl | Et | Me | Me | Me |
| 6-CF₃CH₂O-3-pyridazyl | Et | Me | Me | Me |
| 3-cyclohexyl-phenyl | Et | Me | Me | Me |
| 4-cyclohexyl-phenyl | Et | Me | Me | Me |
| 3-cyclopentyl-phenyl | Et | Me | Me | Me |
| 4-cyclopentyl-phenyl | Et | Me | Me | Me |
| 3-cyclopropyl-phenyl | Et | Me | Me | Me |
| 4-cyclopropyl-phenyl | Et | Me | Me | Me |
| 3-cyclopropyl-phenyl | —(CH₂)₅— | | Me | Me |
| 3-(2,2-Cl₂-cyclopropyl)-phenyl | Et | Me | Me | Me |
| 3-(2,2-F₂-cyclopropyl)-phenyl | Et | Me | Me | Me |
| 3-(cyclopentoxy)-phenyl | Et | Me | Me | Me |
| 4-(cyclopentoxy)-phenyl | Et | Me | Me | Me |
| 3-(cyclopentoxy)-phenyl | —(CH₂)₅— | | Me | Me |
| 4-(cyclopentoxy)-phenyl | —(CH₂)₅— | | Me | Me |
| 3-(cyclohexyloxy)-phenyl | Et | Me | Me | Me |
| 4-(cyclohexyloxy)-phenyl | Et | Me | Me | Me |
| 3-(cyclopropylmethoxy)-phenyl | Et | Me | Me | Me |
| 4-(cyclopropylmethoxy)-phenyl | Et | Me | Me | Me |
| 3-(cyclopropylmethoxy)-phenyl | —(CH₂)₅— | | Me | Me |
| 4-(cyclopropylmethoxy)-phenyl | —(CH₂)₅— | | Me | Me |
| 3-(2,2-Cl₂-cyclopropyl-methoxy)-phenyl | Et | Me | Me | Me |
| 4-2,2-Cl₂-cyclopropyl-methoxy)-phenyl | Et | Me | Me | Me |
| 3-(2,2-F₂-cyclopropyl-methoxy)-phenyl | Et | Me | Me | Me |
| 4-(2,2-F₂-cyclopropyl-methoxy)-phenyl | Et | Me | Me | Me |
| 3-cyclohexylmethoxy-phenyl | Et | Me | Me | Me |
| 5-cyclopentoxy-2-pyridyl | Et | Me | Me | Me |
| 5-(cyclopropylmethoxy)-2-pyridyl | Et | Me | Me | Me |
| 2-cyclopentoxy-5-pyrimidyl | Et | Me | Me | Me |
| 2-(cyclopropylmethoxy)-5-pyrimidyl | Et | Me | Me | Me |
| 5-cyclopentoxy-2-pyrazyl | Et | Me | Me | Me |
| 5-(cyclopropylmethoxy)-2-pyrazyl | Et | Me | Me | Me |
| 6-cyclopentoxy-3-pyridazyl | Et | Me | Me | Me |
| 6-(cyclopropylmethoxy)-3-pyridazyl | Et | Me | Me | Me |

Preferred compounds of general formula (I) are those wherein:

R represents a phenyl, pyridyl, pyrimidyl, pyrazyl or pyridazyl group, all groups substituted by at least a substituent selected from difluoromethoxy, 2,2,2-trifluoroethoxy, 1,1,2,2-tetrafluoroethoxy, 2,2,3,3-tetrafluoropropoxy, 2,2,3,3,3-pentafluoropropoxy, 2,2,3,4,4,4-hexafluorobutoxy, 2,2,3,3,4,4,5,5-octafluoropentoxy, cyclopentoxy, cyclohexyloxy, cyclopropylmethoxy or cyclohexylmethoxy; said phenyl, pyridyl, pyrimidyl, pyrazyl or pyridazyl group being optionally substituted by one or two further substituents, equal to or different from each other, selected from a fluorine atom, a chlorine atom, methyl or trifluoromethyl;

$R_1$ represents ethyl, n-propyl, isopropyl;

$R_2$ represents methyl;

or $R_1$ and $R_2$, together with the N atom to which they are bound, represent a pyrrolidyl, piperidyl or morpholyl group;

$R_3$ and $R_4$ represent methyl.

More preferred compounds of general formula (I) are those wherein:

R represents a phenyl group substituted by at least a substituent selected from difluoromethoxy, 2,2,2-trifluoroethoxy, 1,1,2,2-tetrafluoroethoxy, 2,2,3,3-tetrafluoropropoxy, 2,2,3,3,3-pentafluoropropoxy, 2,2,3,4,4,4-hexafluorobutoxy, 2,2,3,3,4,4,5,5-octa-fluoropentoxy, cyclopentoxy, cyclohexyloxy, cyclopropylmethoxy or cyclohexylmethoxy; said phenyl group being optionally substituted by one or two further substituents, equal to or different from each other, selected from a fluorine atom, a chorine atom, methyl or trifluoromethyl;

R$_1$ represents ethyl, n-propyl, isopropyl;
R$_2$ represents a methyl;
or R$_1$ and R$_2$, together with the N atom to which they are bound, represent a pyrrolidyl, piperidyl or morpholylgroup;
R$_3$ and R$_4$ represent methyl.

The compounds having general formula (I) are prepared from the corresponding aniline having formula (II), according to the following reaction scheme 1:

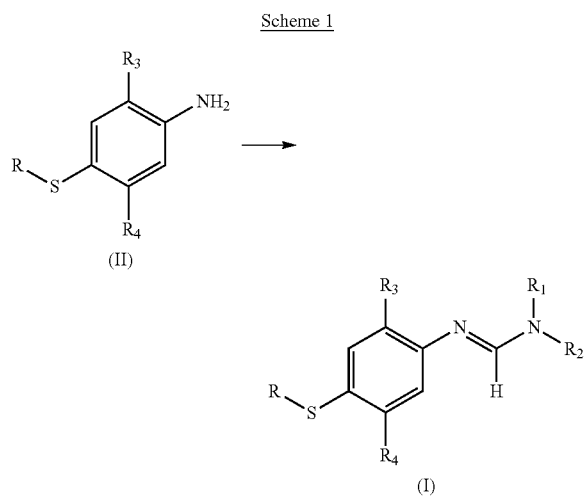

Various methods for effecting this transformation are known in literature; the most widely used methods are the following:

a) treatment of aniline having formula (II) with an acetal having the formula R$_1$R$_2$NC(OR$_5$), wherein R$_5$ represents an alkyl, according to what is described in "Synthetic Communications", 24 (1994), pages 1617-1624;

b) treatment of aniline having formula (II) with an amide having the formula HCONR$_1$R$_2$ in the presence of POCl$_3$ or SOCl$_2$, according to what is described in "Tetrahedron", 46 (1990), pages 6058-6112;

c) treatment of aniline having formula (II) with an orthoester having the formula HC(OR$_5$), wherein R$_5$ represents an alkyl, to form the corresponding imino-ether followed by heating of the same in the presence of an amine having the formula HNR$_1$R$_2$, according to what is described in U.S. Pat. No. 4,209,319;

d) treatment of aniline having formula (II) with phosgene to form the corresponding isocyanate followed by reaction with an amide having the formula HCONR$_1$R$_2$, according to what is described in WO 00/46184;

e) treatment of aniline having formula (II) with C$_2$H$_5$OCH=NCN to form an N-cyanoamidine followed by reaction with an amine having the formula HNR$_1$R$_2$, according to what is described in WO 00/46184;

f) treatment of aniline having formula (II) with N,N-dimethylformamide in the presence of a sulfonyl-chloride, such as for example, 2-pyridylsulfonyl-chloride or phenylsulfonylchloride, to form the corresponding dimethylamidine (R$_1$=R$_2$=Me) followed by reaction with an amine having the formula HNR$_1$R$_2$, according to what is described in "Tetrahedron", 56 (2000), pages 8253-8262 and in "Journal Combinatorial Chemistry", 11 (2009), pages 126-130.

The compound having formula (II) can be prepared by reduction of the corresponding nitro-derivative having formula (III), as indicated in reaction scheme 2, according to methods well-known in organic chemistry, as described for example in "Advanced Organic Chemistry", Jerry March, 4$^a$ Edition, 1992, John Wiley & Sons Pub., pages 1216-1217 and references cited therein.

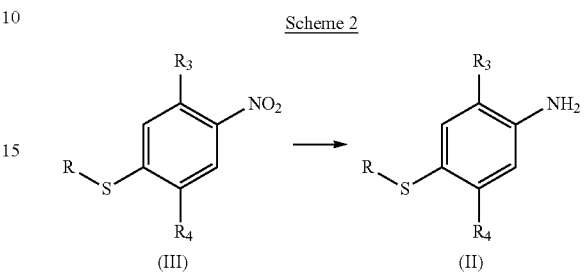

The preferred reaction conditions for these substrates envisage the use of tin chloride in concentrated hydrochloric acid, according to what is described in detail in international patent application WO 00/46184.

The compound having formula (III) can be prepared by reaction of the compound having formula (IV) with a compound having formula RX, wherein X is a leaving group such as, for example, a halogen atom, a mesylate or a tosylate group, in the presence of a base, preferably potassium carbonate or sodium hydride, according to reaction scheme 3:

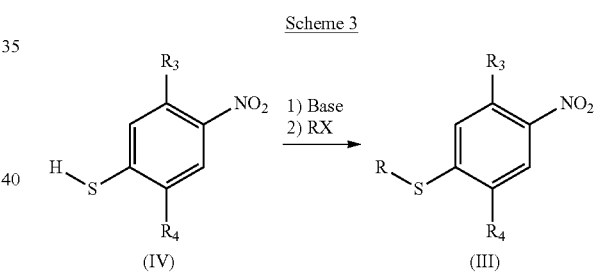

Alternatively, the compound having formula (III) can also be obtained by reaction of the compound having formula (V), wherein Y represents a halogen atom, with a compound having the formula RSH, in the presence of a base, preferably potassium carbonate or sodium hydride, according to reaction scheme 4.

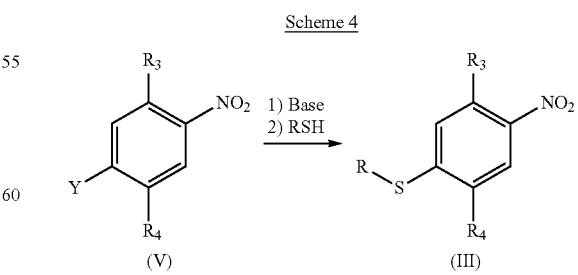

The compounds having formula (IV) are prepared by reacting, in the presence of a palladium catalyst, a compound having formula (V) with potassium thioacetate and subsequently saponifying the thioester thus obtained, according to what is described in "Tetrahedron Letters", 48 (2007), pages 3033-3037.

The compounds having general formula (I) containing polyfluoroalkoxy, (halo)cycloalkoxy or (halo)cycloalkylalkoxy groups on the ring R can also be obtained, by means of known techniques, starting from hydroxy-[(hetero)arylthio] phenylformamidines (obtainable as described in examples 4, 5 and 6) by addition to fluorinated olefins, as described in more detail in example 7, or by etherification with the corresponding halides or tosylates.

As already mentioned, the compounds having general formula (I) have an extremely high fungicidal activity which is exerted with respect to numerous phytopathogenic fungi which attack important agricultural crops.

Examples of phytopathogenic fungi which can be effectively treated and fought with the compounds having general formula (I) are those belonging to the groups of Basidiomycetes, Ascomycetes, Deuteromycetes or imperfect fungi, Oomycetes: *Puccinia* spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides, Colletotrichum* spp., *Pyricularia oryzae, Sclerotium* spp., *Phytophtora* spp., *Pythium* spp., *Plasmopara viticola, Peronospora* spp., *Pseudoperonospora cubensis, Bremia lactucae.*

The main crops which can be protected with the compounds according to the present invention comprise cereals (corn, barley, rye, oats, rice, maize, sorghum, etc.), fruit trees (apples, pears, plums, peaches, almonds, cherries, bananas, vines, strawberries, raspberries, blackberries, etc.), citrus trees (oranges, lemons, mandarin oranges, grapefruits, etc.), leguminous plants (beans, peas, lentils, soybean, etc.), horticultural plants (spinach, lettuce, asparagus, cabbages, carrots, onions, tomatoes, potatoes, aubergines, peppers, etc.), cucurbitaceae (pumpkins, courgettes, cucumbers, melons, watermelons, etc.), oleaginous plants (sunflower, rape, peanut, castor oil plant, coconut, etc.), tobacco, coffee, tea, cacao, sugar beet, sugar cane, cotton.

In particular, the compounds having formula (I) have proved to be extremely effective in the control of *Phytophtora infestans* and *Botrytis Cinerea* on tomatoes; *Puccinia recondita, Erisiphae graminis, Helminthosporium teres, Septoria nodorum* and *Fusarium* spp. on cereals, in the control of *Phakopsora pachyrhizi* on soybean, in the control of *Uromyces Appendiculatus* on beans, in the control of *Venturia inaequalis* on apple trees, in the control of *Sphaerotheca fuliginea* on cucumbers.

Furthermore, the compounds having formula (I) are also effective in the control of bacteria and phytopathogenic viruses, such as for example *Xanthomonas* spp., *Pseudomonas* spp., *Erwinia amylovora*, tobacco mosaic virus.

The compounds having formula (I) are capable of exerting a fungicidal action of both a curative and preventive nature and have an extremely low or zero phytotoxicity on the crops treated.

A further object of the present invention therefore relates to the use of the compounds having formula (I) for the control of phytopathogenic fungi of agricultural crops.

For practical uses in agriculture, it is often preferable to use fungicidal compositions containing the compounds of the present invention suitably formulated.

A further object of the present invention relates to fungicidal compositions comprising one or more compounds having formula (I), a solvent and/or solid or liquid diluent, optionally a surface-active agent.

The above fungicidal compositions can be in the form of dry powders, wettable powders, emulsifying concentrates, emulsions, microemulsions, pastes, granulates, water dispersible granules, solutions, suspensions, etc.: the choice of the type of composition will depend on the specific use.

The fungicidal compositions are prepared in the known way, for example by diluting or dissolving the active substance with a solvent medium and/or a solid or liquid diluent, optionally in the presence of surfactants.

Solid diluents or supports which can be used for example are: silica, kaolin, bentonite, talc, infusorial earth, dolomite, calcium carbonate, magnesia, gypsum, clays, synthetic silicates, attapulgite, sepiolite.

Liquid solvents or diluents which can be used, are for example, in addition to water, aromatic organic solvents (xylols or blends of alkylbenzols, chlorobenzene, etc.), paraffins (petroleum fractions), alcohols (methanol, propanol, butanol, octanol, glycerine, etc.), esters (ethyl acetate, isobutyl acetate, alkyl carbonates, alkyl esters of adipic acid, alkyl esters of glutaric acid, alkyl esters of succinic acid, alkyl esters of lactic acid, etc.), vegetable oils (rape oil, sunflower oil, soybean oil, castor oil, corn oil, peanut oil, and their alkyl esters), ketones (cyclohexanone, acetone, acetophenone, isophorone, ethylamylketone, etc.), amides (N,N-dimethylformamide, N-methylpyrrolidone, etc.), sulfoxides and sulfones (dimethylsulfoxide, dimethylsulfone, etc.), and mixtures thereof.

Sodium salts, calcium salts, potassium salts, salts of triethylamine or triethanolamine of alkylnaphthalenesulfonates, polynaphthalenesulfonates, alkyl sulfonates, aryl sulfonates, alkylaryl sulfonates, polycarboxylates, sulfosuccinates, alkyl sulfosuccinates, ligninsulfonates, alkyl sulfates, can be used as surfactants; as also polyethoxylated fatty alcohols, polyethoxylated alkylphenols, polyethoxylated esters of sorbitol, polypropoxy polyethoxylates (block polymers).

The fungicidal compositions can also contain special additives for particular purposes, such as for example, antifreeze agents such as propylene glycol, or adhesive agents, such as Arabic rubber, polyvinyl alcohol, polyvinyl pyrrolidone, etc.

When desired, other compatible active principles can be added to the fungicidal compositions containing the compounds of general formula (I), such as, for example, fungicides different from those having general formula (I), phytoregulators, antibiotics, herbicides, insecticides, fertilizers and/or mixtures thereof.

Examples of fungicides different from those having general formula (I) which can be included in the fungicidal compositions of the present invention are: acibenzolar, ametoctradin, amisulbrom, ampropylfos, anilazine, azaconazole, azoxystrobin, benalaxyl, benalaxyl-M, benomyl, benthiavalicarb, bitertanol, bixafen, blasticidin-S, boscalid, bromuconazole, bupirimate, buthiobate, captafol, captan, carbendazim, carboxin, carpropamid, chinomethionat, chloroneb, chlorothalonil, chlozolinate, cyazofamid, cyflufenamid, cymoxanil, cyproconazole, cyprodinil, debacarb, dichlofluanid, dichlone, diclobutrazol, diclomezine, dicloran, diclocymet, diethofencarb, difenoconazole, diflumetorim, dimethirimol, dimethomorph, dimoxystrobin, diniconazole, dinocap, dipyrithione, ditalimfos, dithianon, dodemorph, dodine, edifenphos, epoxiconazole, etaconazole, ethaboxam, ethirimol, ethoxyquin, etridiazole, famoxadone, fenamidone, fenaminosulf, fenapanil, fenarimol, fenbuconazole, fenfuram, fenhexamid, fenoxanil, fenpiclonil, fenpropidin, fenpropimorph, fenpyrazamine, fentin, ferbam, ferimzone, fluazinam, fludioxonil, flumetover, flumorph, fluopicolide, fluopyram, fluoroimide, fluotrimazole, fluoxastrobin, fluquinconazole, flusilazole, flusulfamide, flutianil, flutolanil, flutriafol, fluxapyroxad, folpet, fosetylaluminium, fuberidazole, furalaxyl, furametpyr, furconazole, furconazole-cis, guazatine, hexaconazole, hymexazol, hydroxyquinoline sulfate, imazalil, imibenconazole, iminoctadine, ipconazole, iprobenfos, iprodione, isoprothiolane, iprovalicarb, isopyrazam, isotianil, kasugamycin, kresoxim-methyl, mancopper, mancozeb, mandipropamid, maneb, mebenil, mepanipyrim, mepronil, meptyldinocap, metalaxyl, metalaxyl-M, metconazole, methfuroxam, metiram, metominostrobin, metrafenone, metsulfovax, myclobutanil, natamycin, nicobifen, nitrothal-isopropyl, nuarimol, ofurace, orysastrobin, oxadixyl, oxpoconazole, oxycarboxin, pefurazoate, penconazole, pencycuron, penflufen, pentachlorofenol e suoi sali, penthiopyrad, phthalide, picoxystrobin, piperalin, Bordeaux mixture, polyoxins, probenazole, prochloraz, procymidone, propamocarb, propiconazole, propineb, proquinazid, prothiocarb, prothioconazole, pyracarbolid, pyraclostrobin, pyrametostrobin, pyraoxystrobin, pyrazophos, pyribencarb, pyrifenox, pyrimethanil, pyriofenone, pyroquilon, pyroxyfur, quinacetol, quinazamid, quinconazole, quinoxyfen, quintozene, rabenzazole, copper hydroxide, copper oxychloride, copper (I) oxide, copper sulfate, sedaxane, silthiofam, simeconazole, spiroxamine, streptomycin, tebuconazole, tebufloquin, tetra-conazole, thiabendazole, thiadifluor, thicyofen, thifluzamide, thiophanate, thiophanate-methyl, thiram, tiadinil, tioxymid, tolclofosmethyl, tolylfluanid, triadimefon, triadimenol, triarimol, triazbutil, triazoxide, tricyclazole, tridemorf, trifloxystrobin, triflumizole, triforine, triticonazole, uniconazole, uniconazole-P, validamycin, valifenalate, vinclozolin, zineb, ziram, sulfur, zoxamide.

The concentration of phenylamidine compounds having general formula (I) in the above compositions can vary within a wide range; it generally ranges from 1% to 90% by weight with respect to the total weight of the composition, preferably from 5% to 50% by weight with respect to the total weight of the composition.

The application of these compositions can be effected on all parts of the plant, for example on the leaves, stems, branches and roots, or on the seeds themselves before sowing, or on the ground in which the plant grows.

A further object of the present invention therefore relates to a method for the control of phytopathogenic fungi in agricultural crops, which consists in the application of effective dosages of the compounds of formula (I), used as such or formulated in fungicidal compositions as described above.

The quantity of compound to be applied for obtaining the desired effect can vary in relation to different factors, such as, for example, the compound used, the crop to be preserved, the type of pathogen, the degree of infection, the climatic conditions, the application method, the formulation adopted.

Doses of compound ranging from 10 g to 5 kg per hectare of agricultural crop generally provide a sufficient control.

The following examples are provided for a better understanding of the invention for illustrative and non-limiting purposes of the same.

EXAMPLE 1

Preparation of
2-nitro-5-(3-difluoromethoxyphenylthio)-p-xylene
[nitroderivative of formula (III)]

4.36 g (0.109 moles) of sodium hydride are suspended in 80 ml of N,N-dimethylformamide at 0° C. 20 g of 4-nitro-2,5-dimethylthiophenol (0.109 moles) dissolved in 67 ml of N,N-dimethylformamide are added dropwise under stirring. 24.4 g of 1-bromo-3-(difluoromethoxy)benzene (0.109 moles) dissolved in 20 ml of N,N-dimethylformamide are then added dropwise; catalytic Cu° and CuCl are subsequently added and the reaction temperature is brought to 150° C. for 1 h.

After GC control, the reaction mixture is cooled to room temperature, filtered on a celite bed, diluted with water and extracted with ethyl acetate. The organic phase is anhydrified with sodium sulfate, and then filtered and evaporated.

The product thus obtained is purified on silica gel eluting with hexane/ethyl acetate 9:1. 30 g of the desired product are obtained. GC-MS: $M^+=325$

EXAMPLE 2

Preparation of
4-(3-difluoromethoxyphenylthio)-2,5-xylidine
[aniline of formula (II)]

7.7 ml of glacial acetic acid (0.135 moles) are added to a solution of 30 g of 2-nitro-5-(3-difluoromethoxyphenylthio)-p-xylene (0.092 moles) in $H_2O$ (40 ml) and ethanol (400 ml); 34.7 g of Fe in powder form (0.621 moles) are carefully added to the reaction mixture kept under stirring at 60° C. The temperature is brought to 90° C. and the mixture is kept under stirring for 1.5 hours. When the reaction is completed (GC and TLC analyses), the mixture is cooled to room temperature; the solid is filtered on a celite bed. The ethanol is concentrated at reduced pressure. The crude product obtained is washed with a saturated solution of sodium bicarbonate and extracted with ethyl acetate.

The organic phase is washed with $H_2O$, anhydrified on sodium sulfate, filtered and evaporated to give 25 g of the desired product. GC-MS: $M^+=295$

ESEMPIO 3

Preparation of N-ethyl-N-methyl-N'-[4-(3-difluoromethoxyphenylthio)-2,5-xylyl]formamidine [Compound N.1]

Catalytic p-toluenesulfonic acid is added to a mixture of 25 g of 4-(3-difluoromethoxyphenylthio)-2,5-xylidine (0.085 moles) and 141 ml of triethylorthoformiate (0.85 moles). The temperature is brought to reflux and the mixture is kept under stirring for 3 hours. The reaction trend is controlled with TLC (eluent hexane/ethyl acetate 8:2). When the reaction is completed, the mixture is concentrated at reduced pressure and the raw product obtained dissolved in methylene chloride (234 ml); 14.3 ml of N-ethylmethylamine (0.17 moles) are added dropwise. The mixture is kept under stirring for 3 hours at 40° C. and, after TLC control (eluent hexane/ethyl acetate 8:2), is concentrated at reduced pressure. 20 g of the desired product are obtained.

GC-MS: $M^+=364$. $^1$H-NMR (CDCl$_3$) $\delta=1.19$ (t, 3H); 2.20 (s, 3H); 2.28 (s, 3H); 2.97 (s, 3H); 3.35 (bq, 2H); 6.65 (t, 1H); 6.70 (bs, 1H); 6.80 (bs, 1H); 6.85-7.35 (c, 4H); 7.50 (bs, 1H)

EXAMPLE 4

Preparation of
2-nitro-5-(3-hydroxyphenylthio)-p-xylene
[nitroderivative of formula (IV)]

A mixture of 18.9 g of 3-mercaptophenol (0.150 moles), 32.9 g of 2-nitro-5-bromo-p-xylene (0.143 moles) and $K_2CO_3$ (0.143 moles) in 95 ml of N,N-dimethylformamide is stirred at room temperature for 2 hours. A solution of HCl at 10% is added under stirring; the mixture is diluted with $H_2O$ and extracted with ethyl acetate. The organic phase is washed again with water, anhydrified on sodium sulfate, filtered and evaporated. 20 g of solid product are obtained, which is used as such for the subsequent reaction.

GC-MS: $M^+=275$

EXAMPLE 5

Preparation of 4-(3-hydroxyphenylthio)-2,5-xylidine 6.3 ml of glacial acetic acid (0.11 moles) are added to a solution of 20 g of the product obtained in Example 4 (0.076 moles) in 328 ml of ethanol and 33 ml of $H_2O$; 29.7 g of Fe in powder form (0.53 moles) are carefully added to the reaction mixture kept under stirring at 60° C. The temperature is brought to 90° C. and the mixture is kept under stirring for 1.5 hours.

When the reaction is complete (GC and TLC analyses), the mixture is cooled to room temperature; the solid is filtered on a celite bed. The ethanol is concentrated at reduced pressure. The product obtained is washed with a saturated solution of sodium bicarbonate and extracted with ethyl acetate. The organic phase is washed with $H_2O$, anhydrified on sodium sulfate, filtered and evaporated to give 15 g of the desired product.

GC-MS: $M^+=245$

EXAMPLE 6

Preparation of N-ethyl-N-methyl-N'-[4-(3-hydroxyphenylthio)-2,5-xylyl]formamidine Catalytic p-toluenesulfonic acid is added to a mixture of 15 g (0.06 moles) of product obtained as described in Example 5 and 100 ml of triethylorthoformiate (0.6 moles). The temperature is brought to reflux and the mixture kept under stirring for 3 hours. The reaction trend is controlled with TLC (eluent hexane/ethyl acetate 8:2). When the reaction is complete, the reaction mixture is concentrated at reduced pressure and the raw product obtained dissolved in 165 ml of methylene chloride; 10 ml of N-ethylmethylamine are added dropwise. The mixture is kept under stirring for 3 hours at 40° C. After TLC control (eluent hexane/ethyl acetate 8:2), the reaction mixture is concentrated at reduced pressure. 18 g of the desired product are obtained, used as such in example 7.

GC-MS: $M^+=314$

EXAMPLE 7

Preparation of N-ethyl-N-methyl-N'-{4-[3-(1,1,2,2-tetrafluoroethoxy)phenylthio]-2,5-xylyl}formamidine [Compound N. 2]

4.7 g of N-ethyl-N-methyl-N'-[4-(3-hydroxyphenylthio)-2,5-xylyl]formamidine (0.015 moles), obtained as described in Example 6, and 1.0 g of KOH (0.015 moles) are suspended in 43 ml of anhydrous toluene and 198 ml of dimethylsulfoxide. The mixture is cooled to −25° C.; a vacuum is created in the apparatus and tetrafluoroethylene is fed. After an hour, the reaction mixture is brought back to room temperature and controlled by means of TLC (hexane/ethyl acetate 7:3).

The reaction is diluted with water and extracted with ethyl acetate; the organic phase is anhydrified with sodium sulfate and concentrated to give 5.7 g of residue. The crude product thus obtained is purified by means of a silica gel chromatographic column eluting with hexane/ethyl acetate/triethylamine 97:2:1.

GC-MS: $M^+=414$. $^1$H-NMR (CDCl$_3$) δ=1.19 (t, 3H); 2.20 (s, 3H); 2.28 (s, 3H); 2.98 (s, 3H); 3.37 (bq, 2H); 5.85 (tt, 1H); 6.72 (bs, 1H); 6.82 (bs, 1H); 6.85-7.35 (c, 4H); 7.50 (bs, 1H)

EXAMPLE 8

Preparation of compounds N. 3-107

Operating analogously to what is described in the previous examples, the compounds having formula (I) reported in Table 2 were obtained.

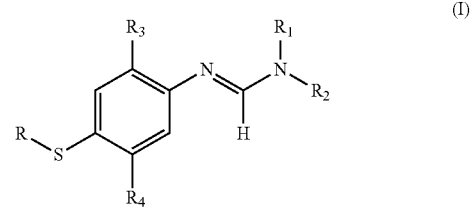

(I)

TABLE 2

| N. | R | R$_1$ | R$_2$ | R$_3$ | R$_4$ |
|---|---|---|---|---|---|
| 3 | 3-HCF$_2$CF$_2$O-phenyl | i-Pr | Me | Me | Me |
| 4 | 3-HCF$_2$CF$_2$O-phenyl | n-Pr | Me | Me | Me |
| 5 | 3-HCF$_2$CF$_2$O-phenyl | —(CH$_2$)$_4$— | | Me | Me |
| 6 | 3-HCF$_2$CF$_2$O-phenyl | —(CH$_2$)$_5$— | | Me | Me |
| 7 | 3-HCF$_2$CF$_2$O-phenyl | —CH$_2$CH$_2$OCH$_2$CH$_2$— | | Me | Me |
| 8 | 4-HCF$_2$CF$_2$O-phenyl | Et | Me | Me | Me |
| 9 | 4-HCF$_2$CF$_2$O-phenyl | —(CH$_2$)$_5$— | | Me | Me |
| 10 | 4-HCF$_2$O-phenyl | Et | Me | Me | Me |
| 11 | 3-HCF$_2$O-phenyl | —(CH$_2$)$_4$— | | Me | Me |
| 12 | 3-HCF$_2$O-phenyl | —(CH$_2$)$_5$— | | Me | Me |
| 13 | 3-HCF$_2$O-phenyl | —CH$_2$CH$_2$OCH$_2$CH$_2$— | | Me | Me |
| 14 | 4-HCF$_2$O-phenyl | —(CH$_2$)$_5$— | | Me | Me |
| 15 | 3-CF$_3$CH$_2$O-phenyl | Et | Me | Me | Me |
| 16 | 3-CF$_3$CH$_2$O-phenyl | —(CH$_2$)$_5$— | | Me | Me |
| 17 | 4-CF$_3$CH$_2$O-phenyl | Et | Me | Me | Me |
| 18 | 4-CF$_3$CH$_2$O-phenyl | —(CH$_2$)$_5$— | | Me | Me |
| 19 | 3-HCF$_2$CF$_2$CH$_2$O-phenyl | Et | Me | Me | Me |
| 20 | 3-HCF$_2$CF$_2$CH$_2$O-phenyl | —(CH$_2$)$_5$— | | Me | Me |
| 21 | 4-HCF$_2$CF$_2$CH$_2$O-phenyl | Et | Me | Me | Me |

TABLE 2-continued

| N. | R | R$_1$ | R$_2$ | R$_3$ | R$_4$ |
|---|---|---|---|---|---|
| 22 | 4-HCF$_2$CF$_2$CH$_2$O-phenyl | —(CH$_2$)$_5$— | | Me | Me |
| 23 | 3-CF$_3$CF$_2$CH$_2$O-phenyl | Et | Me | Me | Me |
| 24 | 3-CF$_3$CF$_2$CH$_2$O-phenyl | —(CH$_2$)$_5$— | | Me | Me |
| 25 | 4-CF$_3$CF$_2$CH$_2$O-phenyl | Et | Me | Me | Me |
| 26 | 4-CF$_3$CF$_2$CH$_2$O-phenyl | —(CH$_2$)$_5$— | | Me | Me |
| 27 | 4-Cl-3-HCF$_2$CF$_2$O-phenyl | Et | Me | Me | Me |
| 28 | 4-Me-3-HCF$_2$CF$_2$O-phenyl | Et | Me | Me | Me |
| 29 | 3-Cl-4-HCF$_2$CF$_2$O-phenyl | Et | Me | Me | Me |
| 30 | 3-Me-4-HCF$_2$CF$_2$O-phenyl | Et | Me | Me | Me |
| 31 | 3-CF$_3$-4-HCF$_2$CF$_2$O-phenyl | Et | Me | Me | Me |
| 32 | 4-Cl-3-HCF$_2$CF$_2$O-phenyl | —(CH$_2$)$_5$— | | Me | Me |
| 33 | 4-Me-3-HCF$_2$CF$_2$O-phenyl | —(CH$_2$)$_5$— | | Me | Me |
| 34 | 3-Cl-4-HCF$_2$CF$_2$O-phenyl | —(CH$_2$)$_5$— | | Me | Me |
| 35 | 3-Me-4-HCF$_2$CF$_2$O-phenyl | —(CH$_2$)$_5$— | | Me | Me |
| 36 | 3-CF$_3$-4-HCF$_2$CF$_2$O-phenyl | —(CH$_2$)$_5$— | | Me | Me |
| 37 | 4-F-3-HCF$_2$CF$_2$O-phenyl | Et | Me | Me | Me |
| 38 | 3-F-4-HCF$_2$CF$_2$O-phenyl | Et | Me | Me | Me |
| 39 | 4-F-3-HCF$_2$CF$_2$O-phenyl | —(CH$_2$)$_5$— | | Me | Me |
| 40 | 3-F-4-HCF$_2$CF$_2$O-phenyl | —(CH$_2$)$_5$— | | Me | Me |
| 41 | 4-Cl-3-HCF$_2$O-phenyl | Et | Me | Me | Me |
| 42 | 3-Cl-4-HCF$_2$O-phenyl | Et | Me | Me | Me |
| 43 | 4-Cl-3-HCF$_2$O-phenyl | —(CH$_2$)$_5$— | | Me | Me |
| 44 | 3-Cl-4-HCF$_2$O-phenyl | —(CH$_2$)$_5$— | | Me | Me |
| 45 | 4-F-3-HCF$_2$O-phenyl | Et | Me | Me | Me |
| 46 | 3-F-4-HCF$_2$O-phenyl | Et | Me | Me | Me |
| 47 | 4-F-3-HCF$_2$O-phenyl | —(CH$_2$)$_5$— | | Me | Me |
| 48 | 3-F-4-HCF$_2$O-phenyl | —(CH$_2$)$_5$— | | Me | Me |
| 49 | 4-Cl-3-CF$_3$CH$_2$O-phenyl | Et | Me | Me | Me |
| 50 | 3-Cl-4-CF$_3$CH$_2$O-phenyl | Et | Me | Me | Me |
| 51 | 4-Cl-3-CF$_3$CH$_2$O-phenyl | —(CH$_2$)$_5$— | | Me | Me |
| 52 | 3-Cl-4-CF$_3$CH$_2$O-phenyl | —(CH$_2$)$_5$— | | Me | Me |
| 53 | 4-F-3-CF$_3$CH$_2$O-phenyl | Et | Me | Me | Me |
| 54 | 3-F-4-CF$_3$CH$_2$O-phenyl | Et | Me | Me | Me |
| 55 | 4-F-3-CF$_3$CH$_2$O-phenyl | —(CH$_2$)$_5$— | | Me | Me |
| 56 | 3-F-4-CF$_3$CH$_2$O-phenyl | —(CH$_2$)$_5$— | | Me | Me |
| 57 | 4-Cl-3-HCF$_2$CF$_2$CH$_2$O-phenyl | Et | Me | Me | Me |
| 58 | 3-Cl-4-HCF$_2$CF$_2$CH$_2$O-phenyl | Et | Me | Me | Me |
| 59 | 4-Cl-3-HCF$_2$CF$_2$CH$_2$O-phenyl | —(CH$_2$)$_5$— | | Me | Me |
| 60 | 3-Cl-4-HCF$_2$CF$_2$CH$_2$O-phenyl | —(CH$_2$)$_5$— | | Me | Me |
| 61 | 4-F-3-HCF$_2$CF$_2$CH$_2$O-phenyl | Et | Me | Me | Me |
| 62 | 3-F-4-HCF$_2$CF$_2$CH$_2$O-phenyl | Et | Me | Me | Me |
| 63 | 4-F-3-HCF$_2$CF$_2$CH$_2$O-phenyl | —(CH$_2$)$_5$— | | Me | Me |
| 64 | 3-F-4-HCF$_2$CF$_2$CH$_2$O-phenyl | —(CH$_2$)$_5$— | | Me | Me |
| 65 | 3-CF$_3$CFHCF$_2$CH$_2$O-phenyl | Et | Me | Me | Me |
| 66 | 3-HCF$_2$CF$_2$CF$_2$CH$_2$O-phenyl | Et | Me | Me | Me |
| 67 | 4-HCF$_2$CF$_2$CF$_2$CH$_2$O-phenyl | Et | Me | Me | Me |
| 68 | 5-HCF$_2$CF$_2$O-2-pyridyl | Et | Me | Me | Me |
| 69 | 5-HCF$_2$O-2-pyridyl | Et | Me | Me | Me |
| 70 | 5-CF$_3$CH$_2$O-2-pyridyl | Et | Me | Me | Me |
| 71 | 5-HCF$_2$CF$_2$CH$_2$O-2-pyridyl | Et | Me | Me | Me |
| 72 | 5-HCF$_2$CF$_2$O-2-pyridyl | —(CH$_2$)$_5$— | | Me | Me |
| 73 | 5-HCF$_2$O-2-pyridyl | —(CH$_2$)$_5$— | | Me | Me |
| 74 | 5-CF$_3$CH$_2$O-2-pyridyl | —(CH$_2$)$_5$— | | Me | Me |
| 75 | 5-HCF$_2$CF$_2$CH$_2$O-2-pyridyl | —(CH$_2$)$_5$— | | Me | Me |
| 76 | 2-HCF$_2$CF$_2$O-5-pyrimidyl | Et | Me | Me | Me |
| 77 | 2-HCF$_2$O-5-pyrimidyl | Et | Me | Me | Me |
| 78 | 5-HCF$_2$CF$_2$O-2-pyrazyl | Et | Me | Me | Me |
| 79 | 5-HCF$_2$O-2-pyrazyl | Et | Me | Me | Me |
| 80 | 5-CF$_3$CH$_2$O-2-pyrazyl | Et | Me | Me | Me |
| 81 | 6-HCF$_2$CF$_2$O-3-pyridazyl | Et | Me | Me | Me |
| 82 | 6-HCF$_2$O-3-pyridazyl | Et | Me | Me | Me |
| 83 | 6-CF$_3$CH$_2$O-3-pyridazyl | Et | Me | Me | Me |
| 84 | 3-cyclohexyloxy-phenyl | Et | Me | Me | Me |
| 85 | 3-cyclohexyloxy-phenyl | —(CH$_2$)$_5$— | | Me | Me |
| 86 | 3-cyclopentoxy-phenyl | Et | Me | Me | Me |
| 87 | 3-cyclopentoxy-phenyl | —(CH$_2$)$_5$— | | Me | Me |
| 88 | 4-cyclohexyloxy-phenyl | Et | Me | Me | Me |
| 89 | 4-cyclohexyloxy-phenyl | —(CH$_2$)$_5$— | | Me | Me |
| 90 | 4-cyclopentoxy-phenyl | Et | Me | Me | Me |
| 91 | 4-cyclopentoxy-phenyl | —(CH$_2$)$_5$— | | Me | Me |
| 92 | 3-cyclopropylmethoxy-phenyl | Et | Me | Me | Me |
| 93 | 3-cyclopropylmethoxy-phenyl | —(CH$_2$)$_5$— | | Me | Me |
| 94 | 4-cyclopropylmethoxy-phenyl | Et | Me | Me | Me |
| 95 | 4-cyclopropylmethoxy-phenyl | —(CH$_2$)$_5$— | | Me | Me |

TABLE 2-continued

| N. | R | R₁ | R₂ | R₃ | R₄ |
|---|---|---|---|---|---|
| 96 | 4-Cl-3-(cyclopropyl-methoxy)-phenyl | Et | Me | Me | Me |
| 97 | 4-F-3-(cyclopropyl-methoxy)-phenyl | Et | Me | Me | Me |
| 98 | 3-cyclohexylmethoxy-phenyl | Et | Me | Me | Me |
| 99 | 5-cyclopentoxy-2-pyridyl | Et | Me | Me | Me |
| 100 | 5-cyclopropylmethoxy-2-pyridyl | Et | Me | Me | Me |
| 101 | 2-cyclopropylmethoxy-5-pyrimidyl | Et | Me | Me | Me |
| 102 | 3-HCF$_2$CF$_2$O-phenyl | Et | Me | Me | H |
| 103 | 3-HCF$_2$CF$_2$O-phenyl | Et | Me | H | Me |
| 104 | 3-HCF$_2$CF$_2$O-phenyl | Et | Me | Me | Cl |
| 105 | 3-HCF$_2$CF$_2$O-phenyl | Et | Me | Cl | Cl |
| 106 | 3-HCF$_2$CF$_2$O-phenyl | Et | Me | Me | MeO |
| 107 | 3-HCF$_2$CF$_2$S-phenyl | Et | Me | Me | Me |

The compounds were obtained as dense oils. The GC-MS (M⁺) and ¹H-NMR (CDCl₃) data for the most representative compounds are reported in Table 3.

TABLE 3

| N. | M⁺ | ¹H—NMR |
|---|---|---|
| 3 | 414 | 1.19 (t, 3H); 2.20 (s, 3H); 2.28 (s, 3H); 2.98 (s, 3H); 3.37 (bq, 2H); 5.85 (tt, 1H); 6.72 (bs, 1H); 6.82 (bs, 1H); 7.05-7.35 (c, 4H); 7.50 (bs, 1H) |
| 4 | 426 | 1.35-1.80 (c, 4H); 2.20 (s, 3H); 2.28 (s, 3H); 3.30-3.50 (m, 4H); 5.85 (tt, 1H); 6.72 (bs, 1H); 6.82 (bs, 1H); 6.85-7.35 (c, 4H); 7.50 (bs, 1H) |
| 5 | 440 | 1.35-1.80 (c, 6H); 2.20 (s, 3H); 2.28 (s, 3H); 3.30-3.50 (m, 4H); 5.85 (tt, 1H); 6.72 (bs, 1H); 6.82 (bs, 1H); 6.85-7.35 (c, 4H); 7.50 (bs, 1H) |
| 6 | 442 | 2.20 (s, 3H); 2.28 (s, 3H); 3.30-3.50 (m, 4H); 3.65-3.85 (m, 4H); 5.85 (tt, 1H); 6.72 (bs, 1H); 6.82 (bs, 1H); 6.85-7.35 (c, 4H); 7.50 (bs, 1H) |
| 7 | 440 | 2.20 (s, 3H); 2.28 (s, 3H); 3.30-3.50 (m, 4H); 3.65-3.85 (m, 4H); 5.85 (tt, 1H); 6.72 (bs, 1H); 6.82 (bs, 1H); 7.05-7.35 (c, 4H); 7.50 (bs, 1H) |
| 8 | 364 | 1.19 (t, 3H); 2.20 s, 3H); 2.28 (s, 3H); 2.97 (s, 3H); 3.35 (bq, 2H); 6.65 (t, 1H); 6.70 (bs, 1H); 6.80 (bs, 1H); 7.05-7.35 (c, 4H); 7.50 (bs, 1H) |
| 10 | 390 | 1.35-1.80 (c, 6H); 2.20 (s, 3H); 2.28 (s, 3H); 3.30-3.50 (m, 4H); 6.65 (t, 1H); 6.70 (bs, 1H); 6.80 (bs, 1H); 6.85-7.35 (c, 4H); 7.50 (bs, 1H) |
| 13 | 390 | 1.35-1.80 (c, 6H); 2.20 (s, 3H); 2.28 (s, 3H); 3.30-3.50 (m, 4H); 6.65 (t, 1H); 6.70 (bs, 1H); 6.80 (bs, 1H); 7.05-7.35 (c, 4H); 7.50 (bs, 1H) |
| 15 | 396 | 1.19 (t, 3H); 2.20 (s, 3H); 2.28 (s, 3H); 2.97 (s, 3H); 3.35 (bq, 2H); 4.25 (q, 2H); 6.72 (bs, 1H); 6.82 (bs, 1H); 6.85-7.35 (c, 4H); 7.50 (bs, 1H) |
| 19 | 428 | 1.19 (t, 3H); 2.20 (s, 3H); 2.28 (s, 3H); 2.97 (s, 3H); 3.35 (bq, 2H); 4.25 (q, 2H); 5.85 (tt, 1H); 6.72 (bs, 1H); 6.82 (bs, 1H); 6.85-7.35 (c, 4H); 7.50 (bs, 1H) |
| 23 | 446 | 1.19 (t, 3H); 2.20 (s, 3H); 2.28 (s, 3H); 2.97 (s, 3H); 3.35 (bq, 2H); 4.25 (q, 2H); 6.72 (bs, 1H); 6.82 (bs, 1H); 6.85-7.35 (c, 4H); 7.50 (bs, 1H) |
| 27 | 448 | 1.19 (t, 3H); 2.20 (s, 3H); 2.28 (s, 3H); 2.98 (s, 3H); 3.37 (bq, 2H); 5.85 (tt, 1H); 6.72 (bs, 1H); 6.82 (bs, 1H); 7.0-7.35 (c, 3H); 7.50 (bs, 1H) |
| 30 | 428 | 1.19 (t, 3H); 2.20 (s, 3H); 2.28 (s, 3H); 2.50 (s, 3H); 2.98 (s, 3H); 3.37 (bq, 2H); 5.85 (tt, 1H); 6.72 (bs, 1H); 6.82 (bs, 1H); 6.95-7.35 (c, 3H); 7.50 (bs, 1H) |
| 31 | 482 | 1.19 (t, 3H); 2.20 (s, 3H); 2.28 (s, 3H); 2.98 (s, 3H); 3.37 (bq, 2H); 5.85 (tt, 1H); 6.72 (bs, 1H); 6.82 (bs, 1H); 6.90-7.40 (c, 3H); 7.50 (bs, 1H) |
| 32 | 474 | 1.35-1.80 (c, 6H); 2.20 (s, 3H); 2.28 (s, 3H); 3.30-3.50 (m, 4H); 6.65 (t, 1H); 6.70 (bs, 1H); 6.80 (bs, 1H); 6.95-7.35 (c, 3H); 7.50 (bs,1H) |
| 37 | 432 | 1.19 (t, 3H); 2.20 (s, 3H); 2.28 (s, 3H); 2.98 (s, 3H); 3.37 (bq, 2H); 5.85 (tt, 1H); 6.72 (bs, 1H); 6.82 (bs, 1H); 7.0-7.35 (c, 3H); 7.50 (bs, 1H) |
| 38 | 432 | 1.19 (t, 3H); 2.20 (s, 3H); 2.28 (s, 3H); 2.98 (s, 3H); 3.37 (bq, 2H); 5.85 (tt, 1H); 6.72 (bs, 1H); 6.82 (bs, 1H); 7.0-7.35 (c, 3H); 7.50 (bs, 1H) |
| 39 | 458 | 1.35-1.80 (c, 6H); 2.20 (s, 3H); 2.28 (s, 3H); 3.30-3.50 (m, 4H); 5.85 (tt, 1H); 6.72 (bs, 1H); 6.82 (bs, 1H); 7.0-7.35 (c, 3H); 7.50 (bs, 1H) |
| 40 | 458 | 1.35-1.80 (c, 6H); 2.20 (s, 3H); 2.28 (s, 3H); 3.30-3.50 (m,4H); 5.85 (tt, 1H); 6.72 (bs, 1H); 6.82 (bs, 1H); 7.0-7.35 (c, 3H); 7.50 (bs, 1H) |
| 41 | 398 | 1.19 (t, 3H); 2.20 (s, 3H); 2.28 (s, 3H); 2.98 (s, 3H); 3.37 (bq, 2H); 6.65 (tt, 1H); 6.72 (bs, 1H); 6.82 (bs, 1H); 7.0-7.35 (c, 3H); 7.50 (bs, 1H) |
| 42 | 398 | 1.19 (t, 3H); 2.20 (s, 3H); 2.28 (s, 3H); 2.98 (s, 3H); 3.37 (bq, 2H); 6.65 (tt, 1H); 6.72 (bs, 1H); 6.82 (bs, 1H); 7.0-7.35 (c, 3H); 7.50 (bs, 1H) |
| 43 | 424 | 1.35-1.80 (c, 6H); 2.20 (s, 3H); 2.28 (s, 3H); 3.30-3.50 (m, 4H); 6.65 (t, 1H); 6.70 (bs, 1H); 6.80 (bs, 1H); 6.95-7.35 (c, 3H); 7.50 (bs, 1H) |
| 45 | 382 | 1.19 (t, 3H); 2.20 (s, 3H); 2.28 (s, 3H); 2.98 (s, 3H); 3.37 (bq, 2H); 6.65 (t, 1H); 6.72 (bs, 1H); 6.82 (bs, 1H); 7.0-7.35 (c, 3H); 7.50 (bs, 1H) |
| 47 | 408 | 1.35-1.80 (c, 6H); 2.20 (s, 3H); 2.28 (s, 3H); 3.30-3.50 (m, 4H); 6.60 (tt, 1H); 6.72 (bs, 1H); 6.82 (bs, 1H); 7.0-7.35 (c, 3H); 7.50 (bs, 1H) |
| 49 | 430 | 1.19 (t, 3H); 2.20 (s, 3H); 2.28 (s, 3H); 2.97 (s, 3H); 3.35 (bq, 2H); 4.25 (q, 2H); 6.72 (bs, 1H); 6.82 (bs, 1H); 6.85-7.35 (c, 3H); 7.50 (bs, 1H) |
| 53 | 414 | 1.19 (t, 3H); 2.20 (s, 3H); 2.28 (s, 3H); 2.97 (s, 3H); 3.35 (bq, 2H); 4.25 (q, 2H); 6.72 (bs, 1H); 6.82 (bs, 1H); 6.90-7.40 (c, 3H); 7.50 (bs, 1H) |
| 57 | 462 | 1.19 (t, 3H); 2.20 (s, 3H); 2.28 (s, 3H); 2.97 (s, 3H); 3.35 (bq, 2H); 4.25 (q, 2H); 5.85 (tt, 1H); 6.72 (bs, 1H); 6.82 (bs, 1H); 6.90-7.35 (c, 3H); 7.50 (bs, 1H) |
| 61 | 446 | 1.19 (t, 3H); 2.20 (s, 3H); 2.28 (s, 3H); 2.97 (s, 3H); 3.35 (bq, 2H); 4.25 (q, 2H); 5.85 (tt, 1H); 6.72 (bs, 1H); 6.82 (bs, 1H); 6.95-7.35 (c, 3H); 7.50 (bs, 1H) |
| 68 | 415 | 1.19 (t, 3H); 2.20 (s, 3H); 2.28 (s, 3H); 2.98 (s, 3H); 3.37 (bq, 2H); 5.85 (tt, 1H); 6.72 (bs, 1H); 6.82 (bs, 1H); 7.10-7.90 (c, 4H) |
| 86 | 382 | 1.19 (t, 3H); 1.50-2.0 (m, 8H); 2.20 (s, 3H); 2.28 (s, 3H); 2.98 (s, 3H); 3.37 (bq, 2H); 4.80 (m, 1H); 6.72 (bs, 1H); 6.83 (bs, 1H); 6.9-7.35 (c, 4H); 7.50 (bs, 1H) |
| 92 | 368 | 0.35 (m, 2H); 0.65 (m, 2H); 1.19 (t, 3H); 1.30 (m, 1H); 2.20 (s, 3H); 2.28 (s, 3H); 2.98 (s, 3H); 3.37 (bq, 2H); 4.90 (s, 2H); 6.72 (bs, 1H); 6.82 (bs, 1H); 6.9-7.35 (c, 4H); 7.50 (bs, 1H) |

EXAMPLE 9

Determination of the Fungicidal Activity in Preventive Application (5 Days) Against *Erysiphe graminis* on Wheat Leaves of wheat plants of the Salgemma variety, grown in pots in a conditioned environment kept at 20° C. and 70% of relative humidity (R.H.), were treated by spraying on both sides of the leaves with the compounds under examination, dispersed in hydroacetonic solutions at 20% by volume of acetone.

After remaining 5 days in a conditioned environment, the plants were infected under dry conditions by shaking over them, in order to distribute the inoculum, plants previously infected by *Erysiphe graminis*.

The plants were then maintained in the same cell, in a humidity-saturated environment and at a temperature ranging from 18 to 24° C. for 12 days.

At the end of this period, the external symptoms of the pathogen appeared and it was therefore possible to proceed with the evaluation of the intensity of the infection, on both the parts treated directly with the products (T), and also on the parts which had developed during the test (NT), by means of a visible percentage evaluation scale of the area of affected leafs; the scale comprises, as extremes, the value 100 (healthy plant) and the value 0 (completely infected plant).

All the compounds N. 1-107 showed a full activity (100%) at a dose of 500 p.p.m

At the same time, the phytotoxicity was evaluated (percentage of leaf necrosis) induced on the wheat plants by the application of the products: in this case, the evaluation scale varies from 0 (completely healthy plant) to 100 (completely necrotized plant).

Table 4 shows the results obtained by effecting the test described with compounds N. 1, 2, 15, 19 and 23, compared with the following reference products described in Table 1 of WO 00/46184:

N,N-dimethyl-N'-[4-(3-trifluoromethylphenoxy)-2,5-xylyl]-formamidine (compound N. 1: CR-1);

N,N-dimethyl-N'-[4-(3-trifluoromethylphenylthio)-2,5-xylyl]-formamidine (compound N. 4: CR-2);

N-ethyl-N-methyl-N'-[4-(3-trifluoromethylphenoxy)-2,5-xylyl]formamidine (compound N. 45: CR-3);

N,N-dimethyl-N'-[4-(3-trifluoromethoxyphenoxy)-2,5-xylyl]formamidine (compound N. 190: CR-4);

N,N-dimethyl-N'-{4-[3-(2,2,2-trifluoroethoxy)phenoxy]-2,5-xylyl}formamidine (compound N. 359: CR-5)

TABLE 4

| Compound | ppm | Activity P5 T | Activity P5 NT | Phytotoxicity % N.F. |
|---|---|---|---|---|
| N. 1 | 125 | 100 | 100 | 0 |
|  | 30 | 100 | 100 | 0 |
| N. 2 | 125 | 100 | 100 | 0 |
|  | 30 | 100 | 100 | 0 |
| N. 15 | 125 | 100 | 100 | 0 |
|  | 30 | 100 | 100 | 0 |
| N. 19 | 125 | 100 | 100 | 0 |
|  | 30 | 100 | 100 | 0 |
| N. 23 | 125 | 100 | 100 | 0 |
|  | 30 | 100 | 100 | 0 |
| CR-1 | 125 | 100 | 90 | 25 |
|  | 30 | 90 | 76 | 15 |
| CR-2 | 125 | 95 | 80 | 0 |
|  | 30 | 78 | 65 | 0 |
| CR-3 | 125 | 100 | 96 | 35 |
|  | 30 | 95 | 85 | 20 |
| CR-4 | 125 | 95 | 90 | 30 |
|  | 30 | 75 | 70 | 15 |
| CR-5 | 125 | 90 | 80 | 30 |
|  | 30 | 70 | 65 | 20 |

The compounds N. 1, 2, 15, 19 and 23 proved to be less phytotoxic and/or more active with respect to the reference products.

EXAMPLE 10

Determination of the Fungicidal Activity in Preventive Application (5 Days) Against *Puccinia recondita* on Wheat Leaves of wheat plants of the Salgemma variety, grown in pots in a conditioned environment kept at 20° C. and 70% of relative humidity (R.H.), were treated by spraying on both sides of the leaves with the compounds under examination, dispersed in hydroacetonic solutions at 20% by volume of acetone.

After remaining 5 days in a conditioned environment, the plants were sprayed on both sides of the leafs with an aqueous suspension of conidia of *Puccinia recondita* (2 mg of inoculum per 1 ml of solution for infection).

After being sprayed, the plants were kept in a humidity-saturated environment at a temperature ranging from 18 to 24° C. for the incubation period of the fungus (1 day).

After this period, the plants were put in a greenhouse with R.H. of 70% and at a temperature of 18-24° C. for 14 days.

At the end of this period, the external symptoms of the pathogen appeared and it was therefore possible to proceed with the evaluation of the intensity of the infection, on both the parts treated directly with the products (T), and also on the parts which had developed during the test (NT), by means of a visible percentage evaluation scale of the area of affected leafs; the scale comprises, as extremes, the value 100 (healthy plant) and the value 0 (completely infected plant).

All the compounds N. 1-107 showed a full activity (100%) at a dose of 500 p.p.m

At the same time, the phytotoxicity was evaluated (percentage of leaf necrosis) induced on the wheat plants by the application of the products: in this case, the evaluation scale varies from 0 (completely healthy plant) to 100 (completely necrotized plant).

Table 5 shows the results obtained by effecting the test described with compounds N. 1, 2, 15, 19 and 23, compared with the following reference products described in Table 1 of WO 00/46184:

N,N-dimethyl-N'-[4-(3-trifluoromethylphenoxy)-2,5-xylyl]-formamidine (compound N. 1: CR-1);

N,N-dimethyl-N'-[4-(3-trifluoromethylphenylthio)-2,5-xylyl]-formamidine (compound N. 4: CR-2);

N-ethyl-N-methyl-N'-[4-(3-trifluoromethylphenoxy)-2,5-xylyl]formamidine (compound N. 45: CR-3);

N,N-dimethyl-N'-[4-(3-trifluoromethoxyphenoxy)-2,5-xylyl]formamidine (compound N. 190: CR-4);

N,N-dimethyl-N'-{4-[3-(2,2,2-trifluoroethoxy)phenoxy]-2,5-xylyl}formamidine (compound N. 359: CR-5)

TABLE 5

| Compound | ppm | Activity P5 T | Activity P5 NT | Phytotoxicity % N.F. |
|---|---|---|---|---|
| 1 | 125 | 100 | 100 | 0 |
|   | 30  | 100 | 100 | 0 |
| 2 | 125 | 100 | 100 | 0 |
|   | 30  | 100 | 100 | 0 |
| 15 | 125 | 100 | 100 | 0 |
|    | 30  | 100 | 100 | 0 |
| 19 | 125 | 100 | 100 | 0 |
|    | 30  | 100 | 100 | 0 |
| 23 | 125 | 100 | 100 | 0 |
|    | 30  | 100 | 100 | 0 |
| CR-1 | 125 | 100 | 90 | 26 |
|      | 30  | 80  | 70 | 14 |
| CR-2 | 125 | 95  | 90 | 0 |
|      | 30  | 68  | 60 | 0 |
| CR-3 | 125 | 100 | 100 | 33 |
|      | 30  | 95  | 85  | 21 |
| CR-4 | 125 | 90  | 85  | 30 |
|      | 30  | 70  | 65  | 20 |
| CR-5 | 125 | 85  | 80  | 25 |
|      | 30  | 65  | 60  | 15 |

The compounds N. 1, 2, 15, 19 and 23 proved to be less phytotoxic and/or more active with respect to the reference products.

The invention claimed is:

1. Phenylamidines having general formula (I):

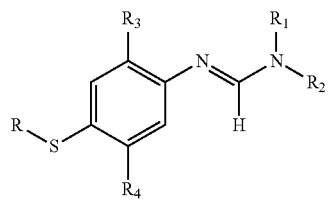

wherein
R represents a phenyl, pyridyl, pyrimidyl, pyrazyl or pyridazyl group, wherein said phenyl, pyridyl, pyrimidyl, pyrazyl or pyridazyl group is substituted by at least a substituent selected from $C_1$-$C_6$ polyfluoroalkoxy containing at least one hydrogen atom, $C_1$-$C_6$ polyfluoroalkylthio containing at least one hydrogen atom, $C_3$-$C_6$ cycloalkyl, $C_3$-$C_6$ halocycloalkyl, $C_3$-$C_6$ cycloalkoxy, $C_3$-$C_6$ halocycloalkoxy, $C_4$-$C_8$ cycloalkylalkoxy, or $C_4$-$C_8$ halocycloalkylalkoxy; said phenyl, pyridyl, pyrimidyl, pyrazyl or pyridazyl being optionally substituted by one or two further substituents, equal to or different from each other, selected from halogen atom, $C_1$-$C_6$ alkyl, or $C_1$-$C_6$ haloalkyl;
$R_1$ represents $C_2$-$C_6$ alkyl;
$R_2$ represents $C_1$-$C_6$ alkyl;
or $R_1$ and $R_2$, together with the N atom to which they are bound, form a heterocyclic ring containing from 4 to 7 atoms, optionally substituted by halogen atoms;
$R_3$ and $R_4$, equal to or different from each other, represent a hydrogen atom, a halogen atom, a $C_1$-$C_6$ alkyl, a $C_1$-$C_6$ alkoxy, a $C_1$-$C_6$ haloalkoxy, a $CF_3$ group, a $CF_2H$ group, a $CFH_2$ group, or a cyano group.

2. The phenylamidines according to claim 1, wherein:
R represents a phenyl, pyridyl, pyrimidyl, pyrazyl or pyridazyl group, wherein said phenyl, pyridyl, pyrimidyl, pyrazyl or pyridazyl group is substituted by at least a substituent selected from difluoromethoxy, 2,2,2-trifluoroethoxy, 1,1,2,2-tetrafluoroethoxy, 2,2,3,3-tetrafluoropropoxy, 2,2,3,3,3-pentafluoropropoxy, 2,2,3,4,4,4-hexafluorobutoxy, 2,2,3,3,4,4,5,5-octafluoropentoxy, cyclopentoxy, cyclohexyloxy, cyclopropylmethoxy or cyclohexylmethoxy; said phenyl, pyridyl, pyrimidyl, pyrazyl or pyridazyl group being optionally substituted by one or two further substituents, equal to or different from each other, selected from a fluorine atom, a chlorine atom, methyl or trifluoromethyl;
$R_1$ represents ethyl, n-propyl, or isopropyl;
$R_2$ represents methyl; or $R_1$ and $R_2$, together with the N atom to which they are bound, represent a pyrrolidyl, piperidyl or morpholyl group;
$R_3$ and $R_4$ represent methyl.

3. The phenylamidines according to claim 1, selected from compounds having general formula (I) wherein:
R represents a phenyl group substituted by at least a substituent selected from difluoromethoxy, 2,2,2-trifluoroethoxy, 1,1,2,2-tetrafluoroethoxy, 2,2,3,3-tetrafluoropropoxy, 2,2,3,3,3-pentafluoropropoxy, 2,2,3,4,4,4-hexafluorobutoxy, 2,2,3,3,4,4,5,5-octa-fluoropentoxy, cyclopentoxy, cyclohexyloxy, cyclopropylmethoxy or cyclohexylmethoxy; said phenyl group being optionally substituted by one or two further substituents, equal to or different from each other, selected from a fluorine atom, a chorine atom, methyl or trifluoromethyl;
$R_1$ represents ethyl, n-propyl, or isopropyl;
$R_2$ represents a methyl; or $R_1$ and $R_2$, together with the N atom to which they are bound, represent a pyrrolidyl, piperidyl or morpholylgroup;
$R_3$ and $R_4$ represent methyl.

4. A fungicidal compositions comprising one or more compounds of formula (I), according to claim 1, in combination with a solvent and/or a solid or liquid diluent, and optionally a surfactant.

5. The compositions according to claim 4, also comprising active principles compatible with the compounds having general formula (I), selected from fungicides other than the compounds having general formula (I), phytoregulators, antibiotics, herbicides, insecticides, fertilizers and/or mixtures thereof, antifreeze agents, or adhesion agents.

6. The compositions according to claim 4, wherein the concentration of compounds having general formula (I) ranges from 1 to 90% by weight with respect to the total weight of the composition, with respect to the total weight of the composition.

7. A method for the control of phytopathogenic fungi of agricultural crops comprising applying an effective amount of a phenylamidine selected from general formula (I):

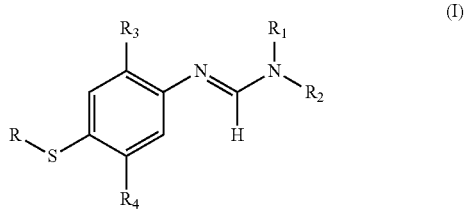

wherein:
R represents a phenyl, pyridyl, pyrimidyl, pyrazyl or pyridazyl group, wherein said phenyl, pyridyl, pyrimidyl, pyrazyl or pyridazyl group is substituted by at least a substituent selected from $C_1$-$C_6$ polyfluoroalkoxy containing at least one hydrogen atom, $C_1$-$C_6$ polyfluoroalkylthio containing at least one hydrogen atom, $C_3$-$C_6$ cycloalkyl, $C_3$-$C_6$ halocycloalkyl, $C_3$-$C_6$ cycloalkoxy, $C_3$-$C_6$ halocycloalkoxy, $C_4$-$C_8$ cycloalkylalkoxy, or $C_4$-$C_8$ halocycloalkylalkoxy; said groups phenyl, pyridyl, pyrimidyl, pyrazyl or pyridazyl being optionally substituted by one or two further substituents, equal to or different from each other, selected from halogen atom, $C_1$-$C_6$ alkyl, or $C_1$-$C_6$ haloalkyl;

$R_1$ represents $C_2$-$C_6$ alkyl;

$R_2$ represents $C_1$-$C_6$ alkyl;

or $R_1$ and $R_2$, together with the N atom to which they are bound, form a heterocyclic ring containing from 4 to 7 atoms, optionally substituted by halogen atoms;

$R_3$ and $R_4$, equal to or different from each other, represent a hydrogen atom, a halogen atom, $C_1$-$C_6$ alkyl, $C_1$-$C_6$ alkoxy, $C_1$-$C_6$ haloalkoxy, a $CF_3$ group, a $CF_2H$ group, a $CFH_2$ group, or a cyano group to phytopathogenic fungi of agricultural crops.

8. A method for the control of phytopathogenic fungi of agricultural crops comprising applying an effective amount of a compound according to claim 2, to phytopathogenic fungi of agricultural crops.

9. A method for the control of phytopathogenic fungi of agricultural crops comprising applying an effective amount of a composition according to claim 4 to phytopathogenic fungi in agricultural crops.

10. A method for the control of phytopathogenic fungi of agricultural crops comprising applying an effective amount of a compound according to claim 7 where said phytopathogenic fungi are selected from the group consisting of Basidiomycetes, Ascomycetes, Deuteromycetes or imperfect fungi, Oomycetes: *Puccinia* spp., *Ustilago* spp., *Tilletia* spp., *Uromyces* spp., *Phakopsora* spp., *Rhizoctonia* spp., *Erysiphe* spp., *Sphaerotheca* spp., *Podosphaera* spp., *Uncinula* spp., *Helminthosporium* spp., *Rhynchosporium* spp., *Pyrenophora* spp., *Monilinia* spp., *Sclerotinia* spp., *Septoria* spp. (*Mycosphaerella* spp.), *Venturia* spp., *Botrytis* spp., *Alternaria* spp., *Fusarium* spp., *Cercospora* spp., *Cercosporella herpotrichoides, Colletotrichum* spp., *Pyricularia oryzae, Sclerotium* spp., *Phytophtora* spp., *Pythium* spp., *Plasmopara viticola, Peronospora* spp., *Pseudoperonospora cubensis*, or *Bremia lactucae*.

11. A method for the control of phytopathogenic fungi of agricultural crops comprising applying an effective amount of a compound to an agricultural crop according to claim 7, wherein the agricultural crop is selected from the group consisting of cereals, fruit trees, citrus trees, leguminous plants, horticultural plants, cucurbitaceae, oleaginous plants, tobacco, coffee, tea, cacao, sugar beet, sugar cane, or cotton.

12. A method for the control of phytopathogenic fungi comprising applying an effective amount of a compound Use according to claim 7 to *Plasmopara viticola* on vines; *Phytophtora infestans* and *Botrytis Cinerea* on tomatoes; *Puccinia recondita, Erysiphe graminis, Helminthosporium teres, Septoria nodorum* and *Fusarium* spp. on cereals; *Phakopsora pachyrhizi* on soybean; *Uromyces Appendiculatus* on beans; *Venturia inaequalis* on apple trees; or *Sphaerotheca fuliginea* on cucumbers.

13. A method for the control of bacteria or phytopathogenic viruses of agricultural crops comprising applying an effective amount of a compound according to claim 1, for the control of bacteria and phytopathogenic viruses.

14. A method for controlling phytopathogenic fungi in agricultural crops, which consists in applying effective dosages of a compound according to claim 1, in amounts ranging from 10 g to 5 kg per hectare of agricultural crop.

15. The compositions according to claim 4, wherein the concentration of compounds having general formula (I) ranges from 5 to 50% by weight with respect to the total weight of the composition.

* * * * *